United States Patent
Sharma

(10) Patent No.: US 9,474,811 B2
(45) Date of Patent: Oct. 25, 2016

(54) METHOD OF TREATING AN EYE INFECTION USING ELECTROMAGNETIC RADIATION IN THE UVC

(76) Inventor: Anant Sharma, Bedford (GB)

( * ) Notice: Subject to any disclaimer, the term of this patent is extended or adjusted under 35 U.S.C. 154(b) by 552 days.

(21) Appl. No.: 13/063,136

(22) PCT Filed: Sep. 9, 2009

(86) PCT No.: PCT/GB2009/002158
§ 371 (c)(1),
(2), (4) Date: May 26, 2011

(87) PCT Pub. No.: WO2010/029292
PCT Pub. Date: Mar. 18, 2010

(65) Prior Publication Data
US 2011/0288617 A1   Nov. 24, 2011

(30) Foreign Application Priority Data
Sep. 9, 2008   (GB) .................................. 0816399.0

(51) Int. Cl.
*A61B 19/00*   (2006.01)
*A61N 5/06*   (2006.01)
*A61L 2/00*   (2006.01)

(52) U.S. Cl.
CPC ........... *A61L 2/0047* (2013.01); *A61N 5/0616* (2013.01); *A61N 5/0624* (2013.01); *A61N 5/0603* (2013.01); *A61N 2005/063* (2013.01); *A61N 2005/0612* (2013.01); *A61N 2005/0642* (2013.01); *A61N 2005/0644* (2013.01); *A61N 2005/0651* (2013.01); *A61N 2005/0661* (2013.01)

(58) Field of Classification Search
CPC ...... A61N 5/06; A61N 5/062; A61N 5/0624; A61N 2005/0642; A61N 2005/065; A61N 2005/0658; A61N 2005/0661
USPC ................. 606/3–6; 128/898; 607/88–93, 96
See application file for complete search history.

(56) References Cited

U.S. PATENT DOCUMENTS

| | | | |
|---|---|---|---|
| 5,871,522 A | 2/1999 | Sentilles | |
| 6,283,986 B1 | 9/2001 | Johnson | |
| 8,414,911 B2 * | 4/2013 | Mattson | A61K 9/0048 424/427 |
| 2002/0035358 A1 * | 3/2002 | Wang | 606/5 |
| 2003/0097122 A1 | 5/2003 | Ganz et al. | |
| 2005/0090722 A1 | 4/2005 | Perez | |
| 2005/0234383 A1 * | 10/2005 | Dougal | A61N 5/06 604/5.02 |
| 2006/0167531 A1 | 7/2006 | Gertner et al. | |
| 2006/0281042 A1 | 12/2006 | Rizoiu et al. | |
| 2007/0167999 A1 * | 7/2007 | Breden et al. | 607/88 |
| 2007/0203550 A1 | 8/2007 | Perez | |
| 2007/0219600 A1 | 9/2007 | Gertner et al. | |
| 2008/0102505 A1 * | 5/2008 | Petrie | A61N 5/06 435/173.3 |
| 2009/0143842 A1 * | 6/2009 | Cumbie | A61N 5/0616 607/88 |
| 2009/0192437 A1 * | 7/2009 | Soltz | A61F 9/008 604/20 |
| 2010/0081185 A1 * | 4/2010 | McDaniel | A61N 5/0616 435/173.1 |

FOREIGN PATENT DOCUMENTS

| | | |
|---|---|---|
| DE | 3502412 A1 | 7/1986 |
| DE | 9201201 U1 | 5/1993 |
| WO | 2005031881 A2 | 4/2005 |
| WO | 2007113537 A1 | 10/2007 |
| WO | 2007136906 A2 | 11/2007 |
| WO | WO 2007/123859 | 11/2007 |

OTHER PUBLICATIONS

International Preliminary Report on Patentability mailed Dec. 29, 2009 issued in corresponding International Application No. PCT/GB2009/002158.
International Search Report mailed Dec. 29, 2009 issued in corresponding International Application No. PCT/GB2009/002158.
Corresponding European Exam Report, Application No. EP 2361116.
EP Communication dated Sep. 16, 2015 in corresponding EP Patent Application No. 09736613.2, 4 pages.

* cited by examiner

*Primary Examiner* — Ahmed Farah
(74) *Attorney, Agent, or Firm* — Carter, DeLuca, Farrell & Schmidt, LLP

(57) ABSTRACT

Infections of body tissues, particularly of the eye or of wounds, are treated by brief low-intensity irradiation with ultraviolet radiation in the UVC band. A suitable treatment device contains a light-emitting diode producing UVC radiation at a wavelength of about 265 nm, at a power output of 5 mW, directed on to a zone of tissue about 4 mm in diameter. An optical aiming system indicates the zone of tissue to be irradiated. Irradiation for periods as brief as 1 second has been found effective, which equates to a dose of 4 mJ/cm$^2$ delivered to the tissue. Longer periods and higher intensities may be used for more resistant infections. Such irradiation may be delivered endoscopically to treat internal infections or to prevent infection during surgery. The device may be hand held or mounted to an ophthalmic slit lamp or other support.

22 Claims, No Drawings

METHOD OF TREATING AN EYE INFECTION USING ELECTROMAGNETIC RADIATION IN THE UVC

CROSS-REFERENCE TO RELATED APPLICATIONS

The present application is a National Stage Entry of International Application No. PCT/GB2009/002158, filed Sep. 9, 2009, which claims the benefit of and priority to British Application No. GB0816399.0, filed Sep. 9, 2008, the entire contents of which are incorporated by reference herein.

The present invention relates to a method and apparatus for promoting healing of body tissues. More particularly but not exclusively, it relates to a method and apparatus for promoting tissue healing with short-wavelength electromagnetic radiation.

Infection of wounds is a significant problem both in surgery and in the treatment of injuries. While antibiotics are available to treat such infections, it is generally important to select the correct antibiotic to treat a particular infective micro-organism. It would be unacceptable merely to dose a patient speculatively, not least due to the rise in antibiotic resistance amongst pathogens. However, waiting until the infection is identified may cause the patient unacceptable suffering.

Other issues with antibiotics and pathogens include the increasing incidence of pathogens with resistance to most antibiotics, such as MRSA (methacillin-resistant *staphylococcus aureus*) and *C.diff* (*clostridium difficile*). Also of relevance, particularly where treatment with less common antibiotics is required, is the sheer cost of a course of treatment. One further problem for some patients is that they may suffer adverse side effects from some antibiotics.

It would thus be beneficial if such infections could be treated by alternative means having broader efficacy, and which could be applied more rapidly once infection has been identified.

In many surgical procedures, it is routine to administer a cocktail of antibiotics in an attempt to forestall post-operative infection. However, this prophylactic approach is likely to incur all the problems referred to above.

Another problem associated with surgery is scarring, both at the surface of the body and within the tissues (including adhesions). Scarring can lead to long-term discomfort and on the skin surface can be unsightly. It is of particular concern in ophthalmic surgery, where post-operative scarring may interfere with vision.

The underlying issue with most forms of scarring is poorly regulated or inappropriate cell growth. Some forms of scar, such as keloid scarring, could be considered as tumourous, although of a benign form. Cancer might also be described as inappropriate cell growth, albeit occurring to a much greater degree. It is therefore envisaged that a treatment effective against scarring might also be effective against cancerous growths or pre-cancerous cells, or to ensure thorough eradication of cancerous material following surgical excision of a tumour or the like.

It is hence an object of the present invention to provide a method and apparatus for treatment of infection, particularly wound infection, and/or to obviate scarring, and/or for treating cancerous growths or cancerous regrowths, which obviates some or all of the above problems.

According to a first aspect of the present invention, there is provided apparatus for treatment of body tissues comprising a source of electromagnetic radiation having a wavelength of between 100 nm and 280 nm and means to direct said electromagnetic radiation to a selected zone of body tissue.

Preferably, said source is adapted to emit electromagnetic radiation having a wavelength of between 200 and 280 nm.

Advantageously, said source is adapted to emit electromagnetic radiation having a wavelength of between 220 and 280 nm.

Said source may be adapted to emit electromagnetic radiation having a wavelength of between 240 and 270 nm.

Said source may be adapted to emit electromagnetic radiation having a wavelength of 265±5 nm.

Said source may be adapted to emit radiation at a plurality of wavelengths.

Said source may be tunable to emit a selected wavelength.

Said source may comprise light-emitting diode means.

Preferably, said source has a power output in the range of 0.005 mW to 50 mW.

Said source may have a power output of 5 mW or less.

Said source may have a power output of at least 0.01 mW.

Optionally, said source may have a maximum power output in the range of 0.1 mW to 1 mW.

The source may be selectably adjustable to emit a desired power output.

Preferably, the apparatus is adapted to irradiate a zone of body tissue having a maximum dimension of 100 mm or less.

Advantageously, the apparatus is adapted to irradiate a zone of body tissue having a maximum dimension of 5 mm or less.

The apparatus may be adapted to irradiate a zone of body tissue having a diameter of no less than 1 mm.

The apparatus may be adapted to irradiate a generally circular zone of body tissue.

The apparatus may be adapted to irradiate a generally annular zone of body tissue.

The apparatus may be adapted to irradiate an elongate zone of body tissue.

The apparatus may be provided with means selectably to adjust a size and/or shape of a zone of irradiated body tissue.

The apparatus may be provided with means to scan said electromagnetic radiation across a zone of body tissue.

Preferably, the apparatus is adapted to produce a radiation intensity of between 0.01 mW/cm² and 500 mW/cm² over said zone of body tissue.

Advantageously, the apparatus is adapted to produce a radiation intensity of no more than 50 mW/cm² over said zone.

The apparatus may be adapted to produce a radiation intensity of no more than 5 mW/cm² over said zone.

Optionally, the apparatus may be adapted to produce a radiation intensity of at least 0.05 mW/cm² over said zone.

In a first embodiment, the apparatus is mounted or mountable to adjustable support means.

The apparatus may then comprise or be mountable to ophthalmic slit lamp means.

In a second embodiment, the apparatus is adapted to be held in a hand of a user.

The apparatus may then comprise integral power supply means, such as electrical storage cell means.

Preferably, the means to direct the electromagnetic radiation comprises optical aiming means.

Advantageously, said aiming means comprises visible illumination means adapted to mark the zone of body tissue to be irradiated.

Said aiming means may comprise means to generate a beam of visible light, such as laser means.

The means to direct the electromagnetic radiation may be adapted to position the apparatus at a preselected distance from the zone of body tissue to be irradiated.

The aiming means may comprise two light beam generating means so convergently aligned that both light beams illuminate the zone of body tissue to be irradiated when the apparatus is at said preselected distance from the zone of the body tissue.

Alternatively or additionally, the means to direct the electromagnetic radiation may comprise light guide means, such as optical fibre means.

The apparatus may then comprise endoscope means.

The apparatus may then be adapted for a user to visualise the zone of body tissue to be irradiated along the same endoscope means as the electromagnetic radiation is passed, and optionally visual illumination is passed.

According to a second aspect of the present invention, there is provided a method for treating an eye infection, comprising the steps of providing a source of electromagnetic radiation having a wavelength of between 100 nm and 280 nm, and irradiating a surface of the eye adjacent the infection with said electromagnetic radiation.

Preferably, said irradiation step is performed for a period and at an intensity sufficient at least partially to inactivate replication of a pathogenic organism.

Said irradiation step may be performed for a period and at an intensity less than that required to kill said pathogenic organism.

Preferably, the method comprises the step of irradiating said surface with electromagnetic radiation having a wavelength of between 200 and 280 nm.

Advantageously, the method comprises the step of irradiating said surface with electromagnetic radiation having a wavelength of between 240 and 270 nm.

Preferably, the method comprises the step of providing a source of said electromagnetic radiation having a power output in the range of 0.005 mW to 50 mW.

Advantageously, said source may have a power output in the range of 0.1 mW to 1 mW.

The method may comprise the step of irradiating a zone of said surface having a maximum dimension of 10 mm or less, optionally having a diameter of 5 mm or less.

The method may comprise the step of irradiating said surface at a radiation intensity of between 0.01 mW/cm$^2$ and 500 mW/cm$^2$.

The method may comprise the step of irradiating said surface at a radiation intensity of 5 mW/cm$^2$ or less.

The method may comprise the step of irradiating said surface at a radiation intensity of at least 0.05 mW/cm$^2$.

The method may comprise performing said irradiation step for no more than 600 seconds.

The method may comprise performing said irradiation step for no more than 30 seconds.

The method may comprise performing said irradiation step for at least 0.01 second.

The method may comprise performing said irradiation step for at least 0.5 second, optionally for 1 second or more.

The method preferably comprises administering a dose of said electromagnetic radiation of 15 J/cm$^2$ or less.

Advantageously, the method comprises administering a dose of said electromagnetic radiation of at least 0.01 mJ/cm$^2$.

The method may comprise administering a dose of said electromagnetic radiation of between 0.1 mJ/cm$^2$ and 1 J/cm$^2$.

The method may comprise administering a dose of at least 1 mJ/cm$^2$.

The method may comprise administering a dose of no more than 250 mJ/cm$^2$.

The method may comprise administering a dose of no more than 15 mJ/cm$^2$.

According to a third aspect of the present invention, there is provided a method for treating infection associated with a wound, comprising the steps of providing a source of electromagnetic radiation having a wavelength between about 100 nm and 280 nm and irradiating said wound and adjacent tissues with said electromagnetic radiation.

Preferably, said irradiation step is performed for a period and at an intensity sufficient at least partially to inactivate replication of a pathogenic organism.

Said irradiation step may be performed for a period and at an intensity less than required to kill said pathogenic organism.

Alternatively, said irradiation step is performed for a period and at an intensity at least sufficient to kill said pathogenic organism.

In a first embodiment, said method comprises the step of irradiating a surgical incision and adjacent surface tissues with said radiation.

Preferably, said irradiation takes place immediately following a surgical procedure.

Additionally or alternatively, said irradiation may take place during said surgical procedure.

The surgical procedure may comprise an ophthalmic procedure.

The method may then comprise the step of irradiating all or part of a surface of the eye with said radiation.

In a second embodiment, the method comprises the step of irradiating at least part of an interior of a surgical incision with said radiation.

Preferably, said irradiation takes place immediately following a surgical procedure, and prior to wound closure.

Additionally or alternatively, the irradiation may take place during said surgical procedure.

Said surgical procedure may be for the purpose of treating an infection of an internal organ of the body.

The surgical procedure may comprise a laparoscopic procedure.

The source of electromagnetic radiation may then comprise endoscope means.

The method may then comprise inserting said endoscope means through a laparoscopic skin incision prior to irradiating the interior of the incision therewith.

In a third embodiment, said method comprises the step of irradiating a non-surgical wound and surrounding tissues with said radiation.

In each of the above embodiments, the source of electromagnetic radiation is preferably adapted to emit said radiation at a wavelength between about 200 nm and 280 nm.

Advantageously, said source is adapted to emit electromagnetic radiation having a wavelength between about 240 nm and 270 nm.

Said source may comprise light-emitting diode means.

According to a fourth aspect of the present invention, there is provided a method for obviating formation of scars and/or adhesions in body tissues, comprising the steps of providing a source of electromagnetic radiation having a wavelength between 100 nm and 280 nm, and irradiating a wound site therewith.

In a first embodiment, the method comprises the step of irradiating a body tissue surface adjacent the wound site.

The method may comprise irradiating a body tissue surface adjacent a surgical incision.

The method may comprise irradiating a surface of an eye adjacent a site of an ophthalmic surgical procedure.

In a second embodiment, the method comprises the step of irradiating an interior of a wound.

The method may comprise the step of irradiating an interior of a surgical incision.

Optionally, the method may comprise the step of irradiating an interior of a laparoscopic incision.

The source of electromagnetic radiation may be adapted to emit radiation having a wavelength of between about 200 nm and 280 nm, optionally between about 240 nm and 270 nm.

Said source may comprise light-emitting diode means.

According to a fifth aspect of the present invention, there is provided a method for treating cancerous or pre-cancerous body tissue, comprising the steps of providing a source of electromagnetic radiation having a wavelength of between about 100 nm and 280 nm and irradiating said body tissue therewith.

Preferably, the method comprises the step of irradiating said body tissue for a period and at an intensity sufficient substantially to inactivate cell replication of said body tissue.

Alternatively, the method may comprise the step of irradiating the cancerous or precancerous body tissue for a period and at an intensity to cause cell damage therein.

The source of electromagnetic radiation may be adapted to emit radiation having a wavelength of between about 200 nm and 280 nm, optionally between about 240 nm and 270 nm.

Said source may comprise light-emitting diode means.

Advantageously, said irradiation step is performed for a period and at an intensity less than that required to kill said pathogenic organism.

According to a sixth aspect of the present invention, there is provided a method for treating an infection in body tissues, comprising the steps of providing a source or sources of electromagnetic radiation having a plurality of wavelengths within the range of 100 nm to 280 nm, and irradiating said body tissues therewith.

The method may comprise irradiating successively at each of said plurality of wavelengths.

Alternatively, the method may comprise irradiating at each of said plurality of wavelengths simultaneously.

According to a seventh aspect of the present invention, there is provided a method for treating an infection in body tissues, comprising the steps of providing a modulated source of electromagnetic radiation having a wavelength of between 100 nm and 280 nm and irradiating said body tissue therewith.

Said source may be adapted for intensity modulation.

Said intensity modulation may comprise a plurality of periods of high-intensity irradiation interspersed with periods of low-intensity or zero irradiation.

Additionally or alternatively, a cross-sectional area of an irradiating beam may be selectably modulated.

Said method may comprise irradiating body tissues with electromagnetic radiation at two or more distinct wavelengths.

In any one of the third to seventh aspects above, the method may comprise any one or more steps as described for the second aspect above.

In any of the second to seventh aspects above, the method may comprise providing apparatus as described in the first aspect above to comprise said source of electromagnetic radiation.

Embodiments of the present invention will now be more particularly described by way of example.

In a first example, a surgical operation is carried out on a cornea of a patient's eye. Subsequently, signs of infection are noted adjacent the operative incision. The cornea and surrounding areas of the eye are irradiated briefly with ultraviolet light in the UVC band (wavelength 100-280 nm). This interferes with the DNA replication of any harmful bacteria or other micro-organisms that may have contaminated the cornea. Similarly, it will interfere with DNA replication of any DNA viruses that may have infected the cornea. As a result, the patient's immune system will be able to deal with these micro-organisms before they can multiply and spread further.

It is also believed that this procedure will reduce the incidence of corneal scarring.

The irradiation is preferably carried out with UVC radiation having a wavelength in the region of 250 to 270 nm, as DNA has an absorption peak at around 260 nm. It is believed that irradiation at this wavelength leads to dimerisation of thymine residues in the DNA helix, interfering with DNA replication. It may not be essential to irradiate sufficiently to kill the bacteria, etc (since this might also cause collateral tissue damage). It will often be sufficient to give the immune system a chance to deal with infection before it becomes established.

Light-emitting diodes (LEDs) emitting radiation in the ultraviolet are now available, and UV LEDs tuned to emit at 265 nm would be highly suitable for these methods. Alternatively, mercury discharge UV lamps are available with an emission peak at 254 nm, which would also be suitable.

There is another DNA absorption peak at around 185 nm, but oxygen is substantially opaque to UV below about 200 nm, so such frequencies would probably need to be used in special atmospheres, or with direct or very close contact between the UV emitter and the tissue to be treated. Also, it is believed that the shorter the wavelength, the shorter the distance it penetrates into tissue.

A suitable treatment device embodying the present invention comprises a light-emitting diode tuned to emit UVC-band electromagnetic radiation at a wavelength of approximately 265 nm. The particular LED used in this example has a power output of 0.5 mW. The device is set up to deliver its UVC radiation into a circular zone of tissue having a diameter of 4 mm, at a separation between the device and the tissue of 8 mm. This thus provides an intensity of irradiation of 4 mW/cm$^2$ across the zone of tissue.

To assist in directing this irradiation to the desired infected zone of tissue, an aiming system is provided. Two low-powered light sources (e.g. low-powered diode lasers) are mounted to the device so that their beams converge at a point 8 mm from the device and in the path of the UVC radiation emitted from the LED. Thus, when a single coincident spot of visible light is seen on the tissue to be treated, this indicates that the device is at the correct distance therefrom, and marks the spot on to which the UVC irradiation will be directed.

In a typical test, irradiation of the infected tissue for no more than 1 second has a major effect on the infection without any collateral harm to the body tissues. This equates to a delivered dose of UVC irradiation of 4 mJ/cm$^2$.

More robust infective organisms require longer periods of irradiation. Periods of at least 30 seconds are possible, without complications, at the above irradiation intensities. This equates to administered doses of UVC of around 120 mJ/cm$^2$.

The UVC irradiation is found to have beneficial effects at lower irradiation intensities, amelioration of infection having been found at UVC source powers as low as 0.012 mW. Over the standard 4 mm diameter irradiated zone of tissue, this equates to an irradiation intensity of approximately 0.1 mW/cm$^2$. The dose administered over a 1 second irradiation period is thus about 0.1 mJ/cm$^2$, while over a 30 second irradiation period, a dose of 3 mJ/cm$^2$ would be delivered to the treated tissues. Evidently, the less intense the irradiation, the longer the period over which it may be administered. At very low intensities, administration over a period of 600 seconds or even more is envisaged.

If essential to extirpate all traces of an infective species, it is believed that significantly higher intensities, longer periods of irradiation and much higher administered doses would be possible without unacceptable side-effects.

The device itself is most conveniently mounted to an adjustable support, such as a conventional ophthalmic slit lamp arrangement. This provides a comfortable rest for the patient's head and allows the device to be located precisely and securely relative to the patient's eye.

An alternative form of the device comprises a hand-held unit, optionally with an integral power supply, such as an electrical storage battery (the power outputs of the UVCLED and the aiming system are such that a mains electrical power supply is unlikely to be required, which makes this form of the device particularly useful for treatment of infection in Less Developed Countries). Although a hand-held device might be less accurately directable, the aiming system will allow sufficient precision for most purposes, particularly since the irradiation levels used are such that no harm is likely to be caused to tissues briefly irradiated in error. In any case, with irradiation periods of no more than a few seconds being required in most cases, keeping the irradiation on target is unlikely to be a problem for the user.

Alternative versions of the device described above would permit irradiation of zones of tissues of other shapes. Annular irradiation zones, or elongate strips, would be of particular use. Optionally, the device may be provided with optics allowing the size and shape of the irradiated zone to be altered as required. Clearly, a UVC source having an adjustable emission power will be useful. Pulsed UVC irradiation, delivering more intense bursts adding up to the same total administered dose, should be applicable. If the instantaneous intensity becomes sufficiently high to affect tissue directly, the duration will be so short as to be below thermal relaxation times of the tissue, and so at worst only the surface cells would be affected.

In a second example, a laparoscopic surgical procedure is carried out. An endoscope provided with a UVC source, ideally a distally-mounted UV LED, is introduced alongside the conventional laparoscopic instruments. The tissues being operated upon are periodically irradiated with UVC, including a final dose at the end of the procedure. Additionally, the laparoscopic incision in the patient's skin and surrounding tissue are irradiated with UVC before being dressed.

This should prevent surface or internal infection, and should also reduce scarring and internal adhesions.

In this case, a UVC-emitting LED, substantially similar to that in the first example, appears to be effective. The UVC irradiation is conveniently directed along the same optical fibre bundle of the endoscope that the surgeon is using to visualise the tissues being operated upon. In this embodiment of the invention, the preferred aiming system comprises a visible light beam passed down the same optical fibre bundle, either coaxially, coincidentally or closely parallelly to the UVC irradiation. Thus, the surgeon may be confident that the tissue marked by the visible light beam will also receive the UVC irradiation (i.e. the device is effectively bore-sighted in this case).

The required irradiation intensities and delivered doses of UVC irradiation in this example are similar to those employed in the first example above.

In a third example, a tumour is irradiated with UVC at an intensity and over a period sufficient to damage its cellular DNA and prevent replication. This should forestall tumour growth and may either on its own or in combination with pharmaceutical treatment lead to destruction of the tumour. The same approach may be used on pre-cancerous tissue to prevent it developing into a full-blown tumour.

UVC irradiation may also be used following excision of a tumour to treat surrounding tissue, in order to deal with any cancerous tissue remaining in situ.

In these cases, longer irradiation periods, higher irradiation intensities and total doses of possibly 1 J/cm$^2$ to 10 J/cm$^2$ or more may be required.

In a fourth example, a patient presents with an infected eye, following damage thereto. It is not immediately clear what the infecting micro-organism might be. The patient's eye is irradiated briefly with ultraviolet light in the UVC band. Whether the infection is bacterial, fungal or any other form, the UVC irradiation will either kill or substantially weaken the infecting micro-organism. The UVC irradiation will thus either treat the infection or attenuate the infection sufficiently for the patient's immune system to deal with it.

The immediate treatment with UVC obviates the need to identify the specific infecting micro-organism and select an appropriate pharmaceutical to combat it. This not only avoids the usual delay in identifying the infection, e.g. from a sample taken by corneal scrape, but also obviates the unfortunately common problem in which the infection cannot be identified, and further samples must be taken and tested.

The apparatus and treatment regime used were very similar to those described in the first example above.

In a fifth example, a patient presents with an infected eye, associated with wearing a contact lens. This may result from insufficient cleaning of the lens, or may be associated with an ischaemic effect, from wearing the lens for too long. The treatment is the same as in the fourth example above, as are the benefits.

In a sixth example, the presence of infection in an internal organ is suspected or has been established. A laparoscopic surgical procedure is then carried out, similar to that in the second example above. An endoscope provided with a UVC source, such as a distally-mounted UV LED and associated light-guide, is introduced alongside the conventional laparoscopic instruments, which are used to access the infected organ. Infected portions of the organ are then irradiated with UVC so as to inactivate or kill the infective organisms under treatment regimes similar to those in the second example above.

In the above examples, irradiation with a single frequency of UVC is described. However, it may be preferable to use more than one frequency; for example, penetration depths into tissue are believed to vary with wavelength. This may be implemented by modulating the wavelength, or by switching between two or more wavelengths, or by irradiating at two wavelengths at the same time.

In the above examples, continuous intensity irradiation is described. However, it may in some circumstances be preferable to employ pulsed irradiation. A sequence of short, high-intensity pulses or flashes may overwhelm the infective organisms more readily while causing less collateral damage to adjacent tissues.

Another irradiation approach would be to modulate the size of an irradiating beam, for example between a tightly focussed, intense beam directed at an identified site of infection, and a broader, more diffuse beam covering an area around said site of infection, to halt any incipient spread of infection therefrom.

The invention claimed is:

1. A method of treating an eye infection, comprising the steps of providing a source of electromagnetic radiation having a wavelength of between 100 nm and 280 nm, and irradiating a surface of the eye adjacent the infection with electromagnetic radiation having a wavelength of between 100 nm and 280 nm, wherein irradiating comprises administering a dose of said electromagnetic radiation of no more than 15 J/cm$^2$.

2. A method of treating an eye infection as claimed in claim 1, wherein said source of electromagnetic radiation has a power output in the range of 0.1 mW to 1 mW.

3. A method of treating an eye infection as claimed in claim 1, comprising the step of irradiating a zone of said surface of the eye adjacent the infection having a maximum dimension of no more than 100 mm.

4. A method of treating an eye infection as claimed in claim 1, comprising the step of irradiating said surface of the eye adjacent the infection at a radiation intensity of between 0.01 mW/cm$^2$ and 500 mW/cm$^2$.

5. A method of treating an eye infection as claimed in claim 1, comprising performing said step of irradiating a surface of the eye adjacent the infection for no more than 600 seconds.

6. A method of treating an eye infection as claimed in claim 1, comprising administering a dose of said electromagnetic radiation of between 0.1 mJ/cm$^2$ and 1 J/cm$^2$.

7. A method of treating an eye infection as claimed in claim 1, comprising the step of irradiating said surface of the eye adjacent the infection with electromagnetic radiation having a wavelength of 265±5 nm.

8. A method of treating an eye infection as claimed in claim 1, comprising the steps of providing a source of electromagnetic radiation having a wavelength of between 265±5 nm and irradiating a surface of the eye adjacent the infection with electromagnetic radiation having a wavelength of 265±5 nm.

9. A method for treating an infection in eye tissue as claimed in claim 1, wherein the source of electromagnetic radiation has a wavelength of between 250 nm and 270 nm.

10. A method for treating an infection in eye tissue as claimed in claim 1, wherein the dose of said electromagnetic radiation is no more than 250 mJ/cm$^2$.

11. A method for treating an infection in eye tissue as claimed in claim 1, wherein the dose of said electromagnetic radiation is no more than 15 mJ/cm$^2$.

12. A method for treating an infection in eye tissue as claimed in claim 1, comprising performing said step of irradiation a surface of the eye adjacent the infection for no more than 30 seconds.

13. A method for treating an infection in eye tissue as claimed in claim 1, comprising the step of irradiating a zone of said surface of the eye adjacent the infection having a maximum dimension of 10 mm or less.

14. A method for treating an infection in eye issue as claimed in claim 1, comprising the step of irradiating a zone of said surface of the eye adjacent the infection having a maximum dimension of 5 mm or less.

15. A method of treating an eye infection, comprising the steps of providing a source of electromagnetic radiation having a wavelength of between 100 nm and 280 nm, and irradiating a surface of the eye adjacent the infection with electromagnetic radiation having a wavelength of between 100 nm and 280 nm, wherein said source of electromagnetic radiation has a power output in the range of 0.1 mW to 1 mW.

16. A method for treating an infection in eye tissue as claimed in claim 15, comprising the step of irradiating said eye tissue with electromagnetic radiation having a wavelength of between 250 nm and 270 nm.

17. A method of treating an eye infection, comprising the steps of providing a source of electromagnetic radiation having a wavelength of between 100 nm and 280 nm, and irradiating a surface of the eye adjacent the infection with electromagnetic radiation having a wavelength of between 100 nm and 280 nm wherein the step of irradiating said surface of the eye adjacent the infection is carried out at a radiation intensity of between 0.01 mW/cm$^2$ and 500 mW/cm$^2$.

18. A method for treating an infection in eye tissue as claimed in claim 17, comprising the step of irradiating said eye tissue with electromagnetic radiation having a wavelength of between 265±5 nm.

19. A method for treating an infection in eye tissue as claimed in claim 17, comprising the step of irradiating said eye tissue with electromagnetic radiation having a wavelength of between 250 nm and 270 nm.

20. A method of treating an infection in eye tissue as claimed in claim 17, wherein the step of irradiating said surface of the eye adjacent the infection is carried out at a radiation intensity of no more than 50 mW/cm$^2$.

21. A method for treating an infection in eye tissue as claimed in claim 17, wherein the step of irradiating said surface of the eye adjacent the infection is carried out at a radiation intensity of no more than 5 mW/cm$^2$.

22. A method for treating an infection in eye tissue as claimed in claim 17, comprising performing said step of irradiating a surface of the eye adjacent the infection for no more than 30 seconds.

* * * * *